United States Patent [19]

Aradate et al.

[11] Patent Number: 5,684,855
[45] Date of Patent: Nov. 4, 1997

[54] X-RAY CT SCANNER

[75] Inventors: Hiroshi Aradate, Otawara; Tatsuro Suzuki, Utsunomiya, both of Japan

[73] Assignee: Kabushiki Kaisha Toshiba, Kawasaki, Japan

[21] Appl. No.: 602,027

[22] Filed: Feb. 15, 1996

[30] Foreign Application Priority Data

Feb. 16, 1995 [JP] Japan .................... 7-028313

[51] Int. Cl.$^6$ .................................................. G21K 11/12
[52] U.S. Cl. ............................. 378/4; 378/145; 378/7
[58] Field of Search .......................... 378/19, 4, 147, 378/145, 7

[56] References Cited

U.S. PATENT DOCUMENTS

| | | | |
|---|---|---|---|
| 4,630,202 | 12/1986 | Mori | 364/414 |
| 5,386,446 | 1/1995 | Fujimoto et al. | 378/20 |
| 5,430,783 | 7/1995 | Hu et al. | 378/4 |

*Primary Examiner*—Don Wong
*Attorney, Agent, or Firm*—Oblon, Spivak, McClelland, Maier & Neustadt, P.C.

[57] ABSTRACT

Only an umbra of an X-ray beam is allowed to enter a designated detecting device arrays of an X-ray detector, whereby stable and good X-ray detection signals and images are provided. Even if a focal spot in an X-ray tube shifts, occurrence of artifacts or shifts of CT numbers is prevented to improve image quality. An X-ray CT scanner comprises an X-ray tube and X-ray detector, which are opposed to each other with a patient lying down on a couchtop between them, and a pre-collimator inserted between the X-ray tube and patient for restricting the width in a slice direction of an X-ray beam irradiated by the X-ray tube. The X-ray detector consists of, for example, a two-dimensional detector in which a plurality of detecting device arrays are arranged in the slice direction, each detecting device array including a plurality of detecting channels. The scanner further comprises a unit for controlling the pre-collimator in a manner that a detecting device array designated among the plurality of detecting device arrays receives only an umbra of the X-ray beam. An X-ray CT image is reconstructed using data detected by the designated detecting device arrays.

20 Claims, 14 Drawing Sheets

X-RAY CT SCANNER

BACKGROUND OF THE INVENTION

1. Field of the Invention

The present invention relates to an X-ray computed tomography (hereinafter CT) scanner, or more particularly, to an X-ray CT scanner having a collimator for restricting the thickness in a slice direction of an X-ray beam that is irradiated by an X-ray tube, transmitted through a patient, and then enters an X-ray detector.

2. Description of the Related Art

In general, an X-ray CT scanner for medical use has a collimator for restricting the thickness in a slice direction of an X-ray beam. The collimator falls into a pre-collimator fulfilling the major function and a post-collimator used on a supplemental basis.

In the X-ray CT scanner, an X-ray beam irradiated by an X-ray tube is collimated to be a fan-shaped beam permitting a slice thickness requested for scanning, the fan beam is transmitted through a patient, and then the transmitted beam is received by an X-ray detector. The pre-collimator is used as an X-ray beam limiting device for beam restriction in a slice direction. Specifically, a pre-collimator 100 has, as shown in FIG. 1, a slit-like aperture, and is interposed between an X-ray tube 101 and a patient 102. A control mechanism 103 is used to adjust the aperture, whereby an X-ray beam XB is reshaped into a fan beam permitting a desired slice thickness. The fan beam transmitted through the patient 102 enters an X-ray detector 104. Based on the detected values, image reconstruction is carried out. The post-collimator also has a slit-like aperture. However, the mounting position of the post-collimator is in the vicinity of the X-ray detector and between the patient and X-ray detector. The post-collimator more finely restricts the thickness in the slice direction of a fan beam collimated by the pre-collimator if necessary.

A focal spot in an X-ray tube has a certain size in a slice direction but is not infinitesimal. When a pre-collimator is used to perform pre-collimation on an X-ray beam, the intensities in the slice direction (profile PL) of an X-ray fan beam entering an X-ray detector are plotted in trapezoidal form as shown in FIG. 2. An area $R_M$ with a constant intensity (hereinafter umbra) and areas $R_S$ (hereinafter penumbrae) lying at both ends in the slice direction of the umbra and having inclining intensities are therefore created.

Thus, an X-ray profile consists of an umbra $R_M$ and penumbrae $R_S$. In a known scanner, an X-ray detector receives all the umbra $R_M$ and penumbrae $R_S$. For example, in single-slice CT, a single-slice detector in which one array of detecting devices is arranged in a channel direction orthogonal to the slice direction is utilized. Normally, as shown in FIG. 2, the positional relationships among the X-ray tube 101 (focal spot F), pre-collimator 100, and single-slice detector 104 are set so that condition (1) "X-ray beam width in slice direction<Detector width in slice direction" can be satisfied. In multi-slice CT, a two-dimensional detector in which two or more arrays of detecting devices are arranged in the channel direction orthogonal to the slice direction is utilized. Even in this case, as shown in FIG. 3, the above condition (1) is kept satisfied. The two-dimensional detector conceptually includes an image intensifier.

For producing images using an X-ray CT scanner, two kinds of data; that is, calibration data and patient data representing actual clinical records, must be acquired. The calibration data is used to compensate for variations in sensitivity among segments of an X-ray detector. The calibration data is X-ray transmission data provided by conducting a measurement at intervals of a relatively long period (for example, weekly or every ten days) using, for example, a well-known phantom. In the process of data processing during patient data acquisition, the calibration data is used for the above sensitivity compensation.

However, an X-ray profile makes a parallel movement in a slice direction from a state indicated with a solid line in FIG. 4 to a state indicated with a dashed line. This is attributable to, for example, expansion caused by the heat generated by electron impingement of an anode of an X-ray tube, or a shift of a focal spot F caused by a backlash or deformation of the anode. Thus, the X-ray profile produced during calibration data acquisition differs from that produced during patient data acquisition. This disables proper sensitivity compensation, thus posing a problem that a reconstructed image contains artifacts or has CT numbers shifted.

The foregoing problem will be described with reference to examples shown in FIGS. 5 and 6. FIG. 5 shows the influence of a change in a slice direction of an X-ray profile relative to a single-slice detector. A total output of the detector is an integral of the product between the X-ray profile in the slice direction and the sensitivity of the detector. When an X-ray profile changes, for example, from a state indicated with a solid line in FIG. 5 to a state indicated with a dotted line during the time between calibration data acquisition and patient data acquisition, if the detector sensitivity in the slice direction is not uniform as illustrated (it is normally not uniform), the detector output varies.

FIG. 6 shows the influence of a change in a slice direction of an X-ray profile relative to a two-dimensional detector. For the two-dimensional detector, when the X-ray profile changes, for example, from a state indicated with a solid line in FIG. 6 to a state indicated with a dotted line during the time between calibration data acquisition and patient data acquisition, the intensities of X rays in detecting device arrays coincident with penumbrae vary greatly.

As mentioned above, the change of an X-ray profile during the time between calibration data acquisition and patient data acquisition causes artifacts. Moreover, since CT numbers are deviated from actual numbers, the change of an X-ray profile eventually brings about such a situation that image quality as well as diagnostic ability deteriorates.

When condition (1) is satisfied as shown in FIG. 3, penumbrae are also used for imaging. This poses a problem that the images of slice sections detected using the penumbrae are inferior in quality to those detected using an umbra.

SUMMARY OF THE INVENTION

The present invention attempts to solve the aforesaid problems existing in the related art. A first object of the present invention is to prevent the deterioration in image quality attributable to the use of penumbrae.

A second object of the present invention is to eliminate artifacts or deviations of CT numbers attributable to a movement in a slice direction of an X-ray profile resulting from a shift of a focal spot, and to produce images of high quality and high precision.

To accomplish the above objects, as one aspect of the invention, an X-ray CT scanner comprises an X-ray tube irradiating an X-ray beam toward an object to be scanned; a pre-collimator being interposed between the X-ray tube and the object and collimating a width of the X-ray beam in a slice direction perpendicular to a cross section of the object sliced by the X-ray beam; an X-ray detector receiving the X-ray beam transmitted through the object and consisting of a two-dimensional detector in which a plurality of detecting element arrays are arranged in the slice direction, each detecting element array including a plurality of detecting channels; means for controlling the pre-collimator in a manner that a detecting element array designated among the plurality of detecting element arrays receives only an umbra of the X-ray beam, the umbra being formed by the pre-collimator together with penumbrae on a profile of the X-ray beam; and means for reconstructing an X-ray CT image on the basis of data detected by the designated element array.

It is preferred that the X-ray CT scanner further comprises a tabletop for laying the object thereon, the tabletop being movable in the slice direction; means for determining a moving distance of the tabletop for every scan of the X-ray beam under a multi scan manner, the moving distance coinciding with a total slice width of the designated detecting element array; and means for controlling movement of the tabletop on the basis of the moving condition determined by the determining means.

It is also preferred that the X-ray CT scanner further comprises: a tabletop for laying the object thereon, the tabletop being movable in the slice direction; means for determining a moving distance of the tabletop for every one rotation of the X-ray tube and the X-ray detector around the object under a helical scan in association with a total width of the designated detecting element array in the slice direction; and means for controlling movement of the tabletop on the basis of the moving distance determined by the determining means.

It is still preferred that the X-ray CT scanner further comprises means for widely setting an aperture width of the pre-collimator in the slice direction by a quantity corresponding to a predictable maximum quantity of movement of the X-ray beam in the slice direction depending on movement of an X-ray focal spot of the X-ray tube.

It is still preferred that the X-ray CT scanner further comprises means for detecting a quantity corresponding to movement of an X-ray focal spot of the X-ray tube, wherein the controlling means includes means for controlling at least one of an aperture width of the pre-collimator in the slice direction, a position of the pre-collimator in the slice direction, and a position of a focal spot of the X-ray tube in the slice direction on the basis of the quantity detected by the detecting means in a manner such that at least the designated detecting element array receives the umbra of the X-ray beam.

As another aspect of the invention, an X-ray CT scanner comprises an X-ray tube irradiating an X-ray beam toward an object to be scanned; a pre-collimator being interposed between the X-ray tube and the object and collimating a width of the X-ray beam in a slice direction perpendicular to a cross section of the object sliced by the X-ray beam; an X-ray detector receiving the X-ray beam transmitted through the object and consisting of a two-dimensional detector in which a plurality of detecting element arrays are arranged in the slice direction, each detecting element array including a plurality of detecting channels; and means for reconstructing an X-ray CT image on the basis of data detected by at least one detecting element array of the plurality of detecting element arrays, the at least one detecting element array receiving only an umbra of the X-ray beam, the umbra being formed by the pre-collimator together with penumbrae on a profile of the X-ray beam.

As still another aspect of the invention, an X-ray CT scanner comprises an X-ray tube irradiating an X-ray beam toward an object to be scanned; a pre-collimator being interposed between the X-ray tube and the object and collimating a width of the X-ray beam in a slice direction perpendicular to a cross section of the object sliced by the X-ray beam; an X-ray detector receiving the X-ray beam transmitted through the object and consisting of a two-dimensional detector in which a plurality of detecting element arrays are arranged in the slice direction, each detecting element array including a plurality of detecting channels; means for selecting either one of a first acquisition mode under which image reconstruction is carried out using data detected by at least one array of the plurality of detecting element arrays, an only umbra of the X-ray beam entering into the at least one array of the plurality of detecting element arrays in the first acquisition mode, the umbra being formed by the pre-collimator together with penumbrae on a profile of the X-ray beam, and a second acquisition mode under which image reconstruction is carried out using data detected by at least one array of the plurality of detecting element arrays, both the umbra and the penumbrae entering into the at least one array of the plurality of detecting element arrays in the second acquisition mode; and means for performing scanning with the X-ray beam in order to acquire the data depending on the acquisition mode selected by the selecting means. It is preferred that the X-ray CT scanner further comprises means for controlling a collimating condition of the pre-collimator in accordance with the selected mode.

The X-ray detector is, for example, a two-dimensional detector in which a plurality of detecting element arrays each including a plurality of detecting channels are arranged in a channel direction orthogonal to the slice direction. The X-ray detector is, for example, a single-slice detector in which one detecting element array including a plurality of detecting channels is arranged in the channel direction orthogonal to the slice direction.

The aperture width and/or position in a slice direction of a pre-collimator are controlled so that the umbra of an X-ray beam will enter an X-ray detector over the width in the slice direction of the X-ray detector. Therefore, even if a focus shift occurs, the intensities of X rays in the slice direction remain constant, and image quality does not deteriorate.

The aperture width in the slice direction of the pre-collimator is set so that the width will be larger than the width of the X-ray detector in the slice direction by a predictable maximum magnitude of a movement of an X-ray beam in the slice direction resulting from a shift of a focal spot in an X-ray tube and that part of the umbra of the X-ray beam will enter the X-ray detector over the whole width in the slice direction of the X-ray detector. Once the aperture is set this way, good signals and image quality are available.

Furthermore, a quantity corresponding to a shift of the focal spot in the X-ray tube is detected, and the aperture width and/or position in the slice direction of the pre-collimator are controlled on the basis of the detected quantity so that the umbra of an X-ray beam will enter the X-ray detector over the width in the slice direction of the X-ray detector. Therefore, even if the magnitude of a shift of the focal spot changes during the time between calibration data acquisition and scanning, the umbra of an X-ray beam enters the X-ray detector without fail. Stable and good calibration can therefore be achieved during image reconstruction. Eventually, occurrence of artifacts or shifts of CT numbers can be prevented.

DETAILED DESCRIPTION OF THE PREFERRED EMBODIMENTS

An X-ray CT scanner in accordance with an embodiment of the present invention will be described with reference to FIGS. 7 to 18.

Figure 1:
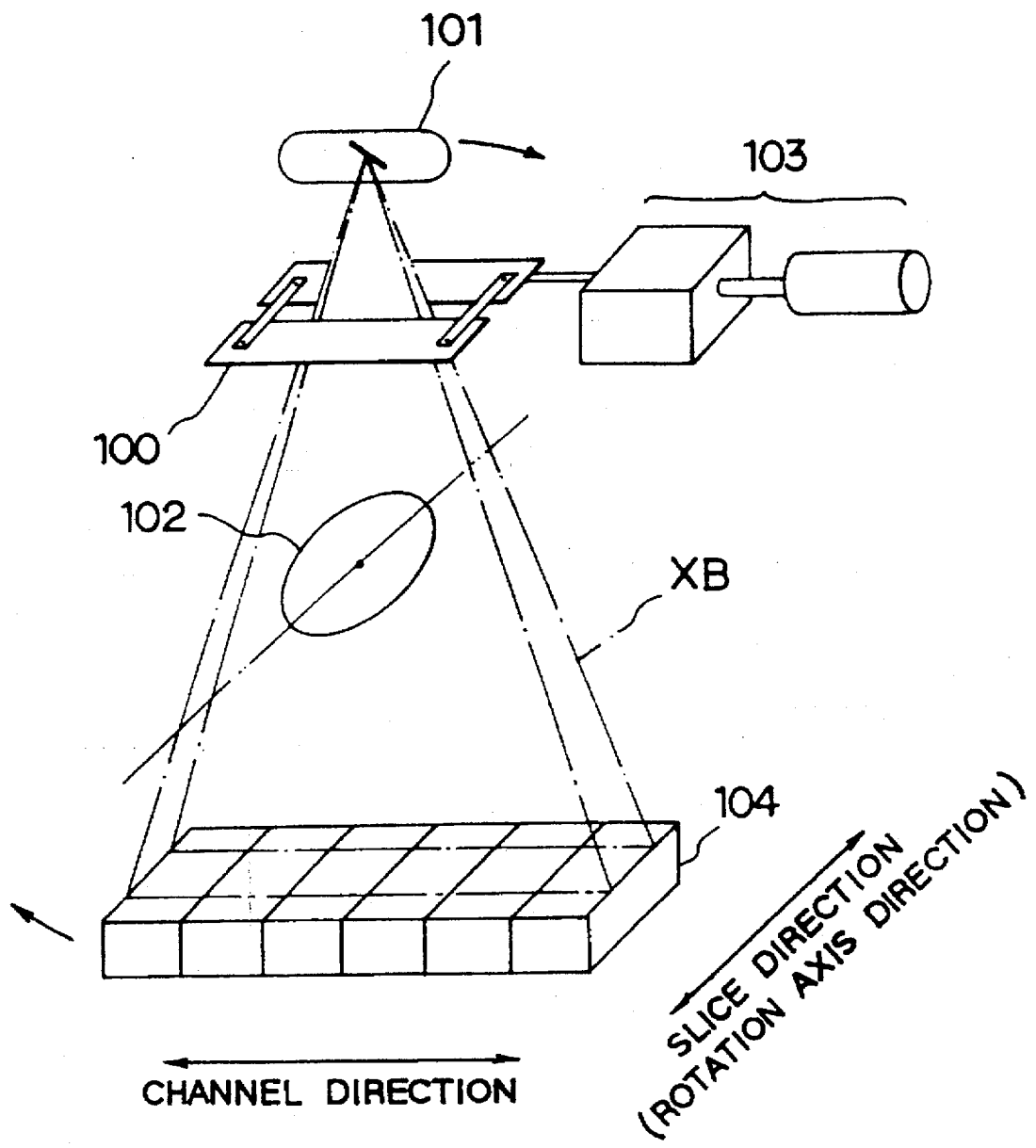
FIG. 1 is a diagram for explaining the role of the pre-collimator.
Figure 2:
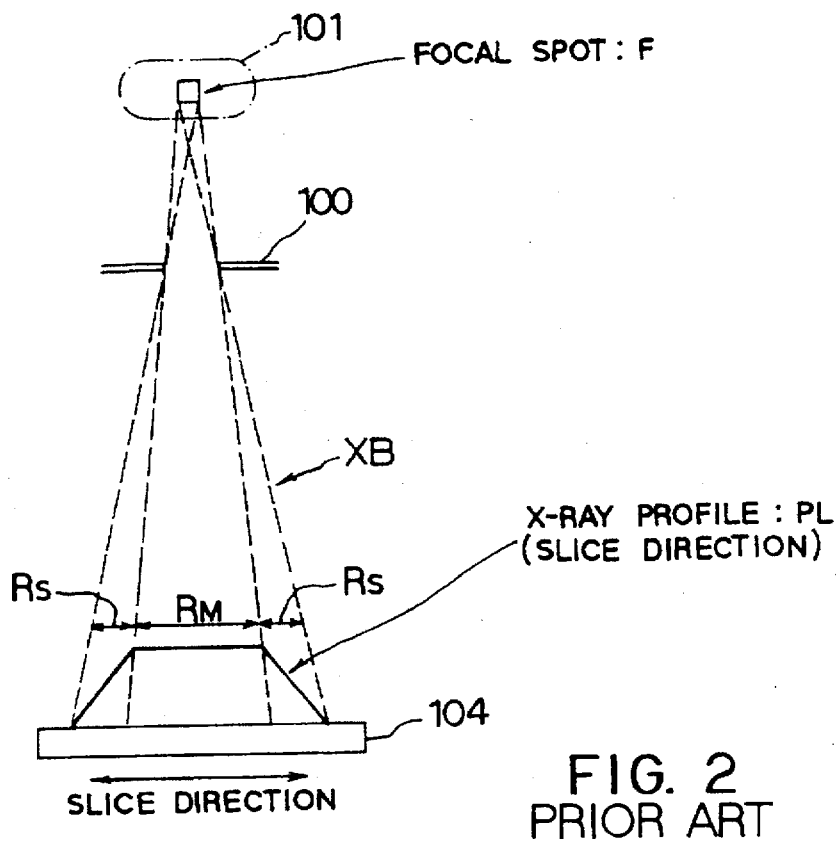
FIG. 2 is a diagram for explaining the positional relationship between an X-ray profile and X-ray detector in known single-slice CT.
Figure 3:
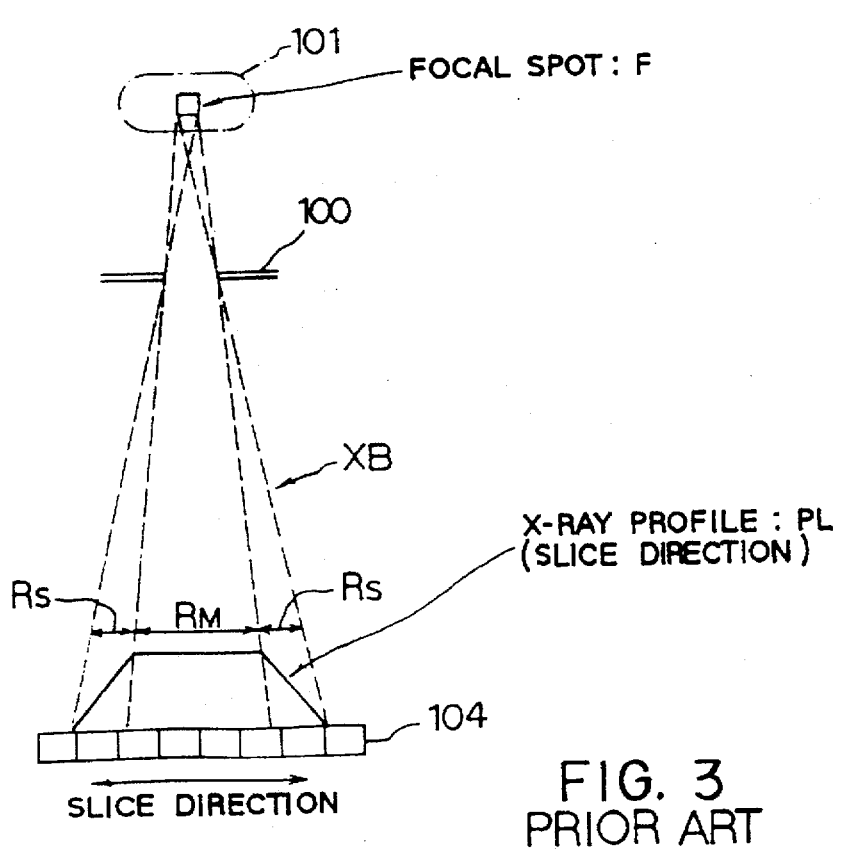
FIG. 3 is a diagram for explaining the positional relationship between an X-ray profile and X-ray detector in CT in which a known two-dimensional detector is employed.
Figure 4:
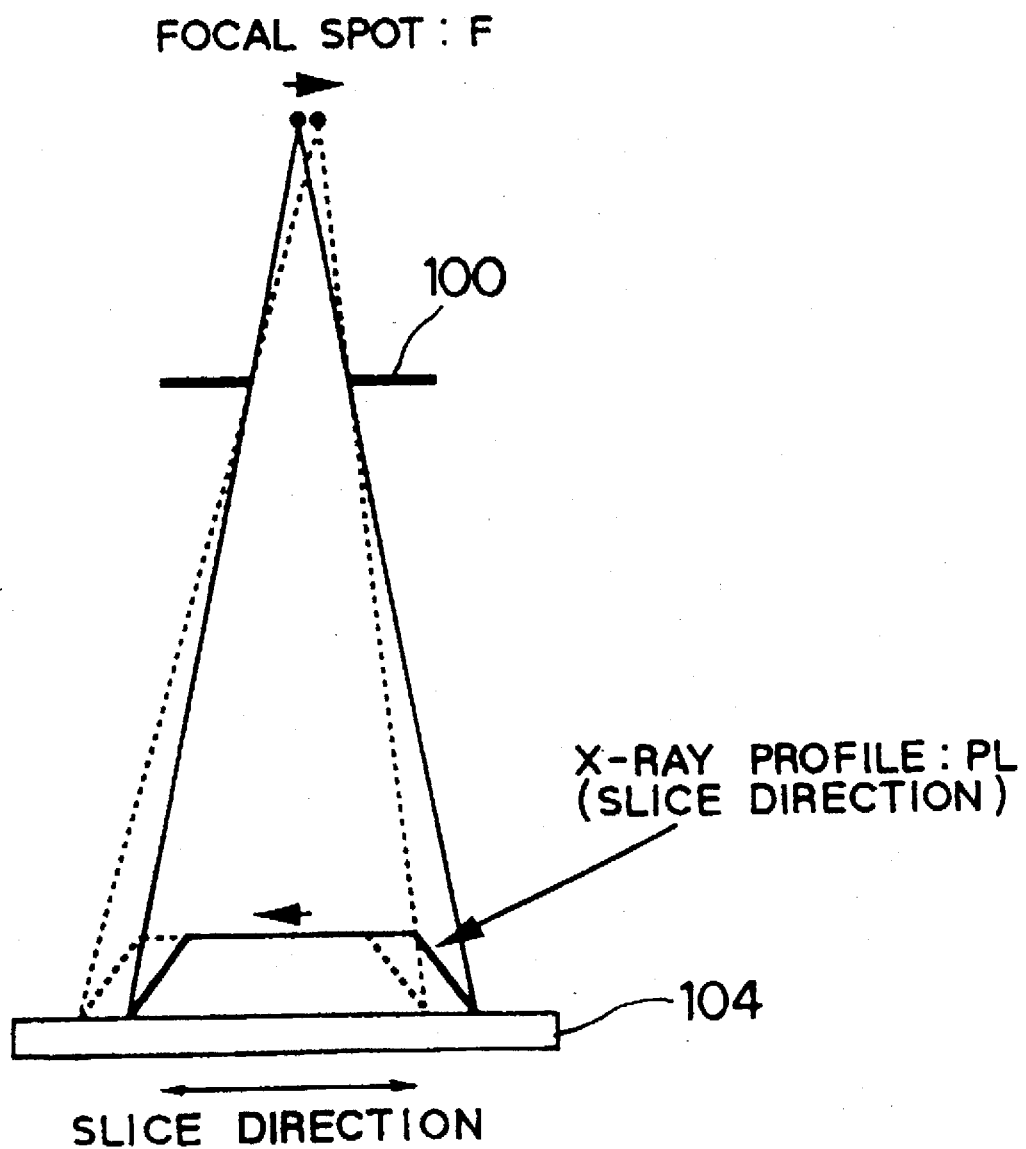
FIG. 4 is a diagram for explaining a shift of a focal spot in an X-ray tube.
Figure 5:
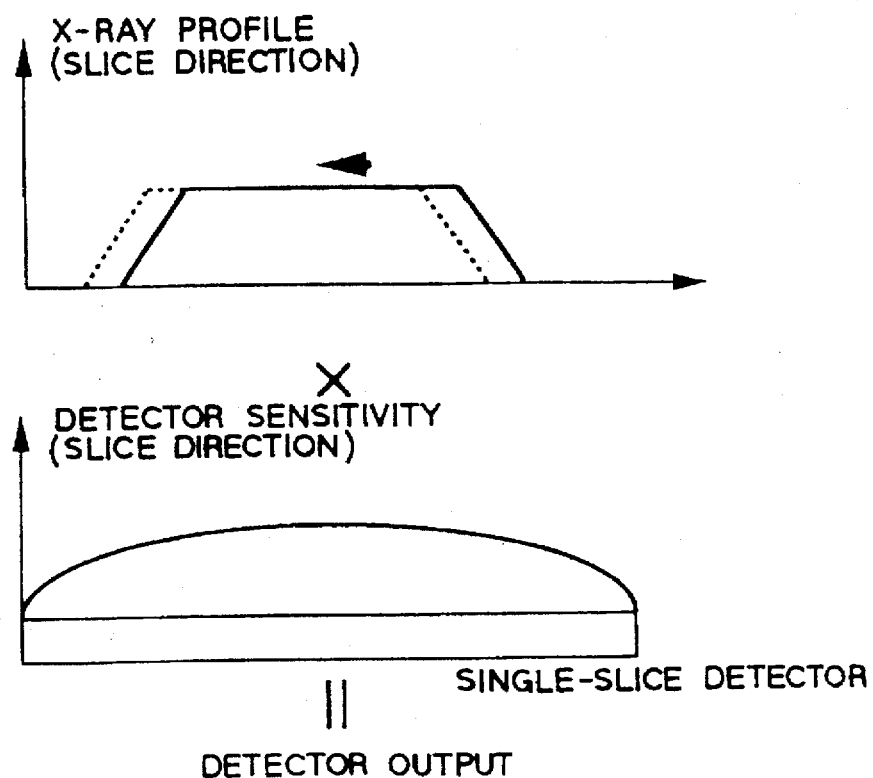
FIG. 5 is a diagram for explaining the influence of a change in profiles upon a single-slice detector.
Figure 6:
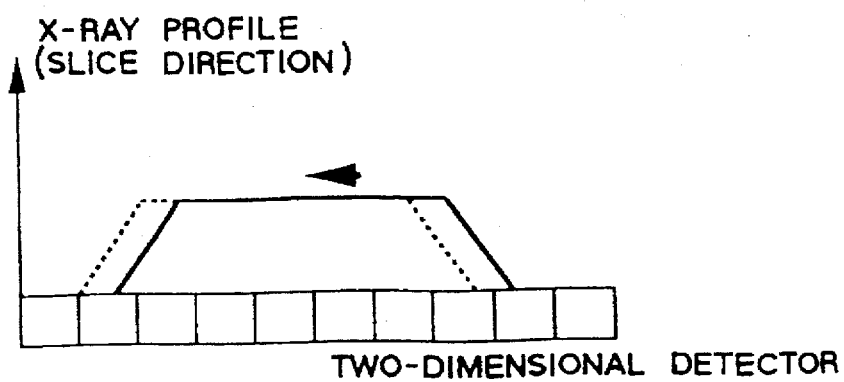
FIG. 6 is a diagram for explaining the influence of a change in profiles upon a two-dimensional detector.
Figure 7:
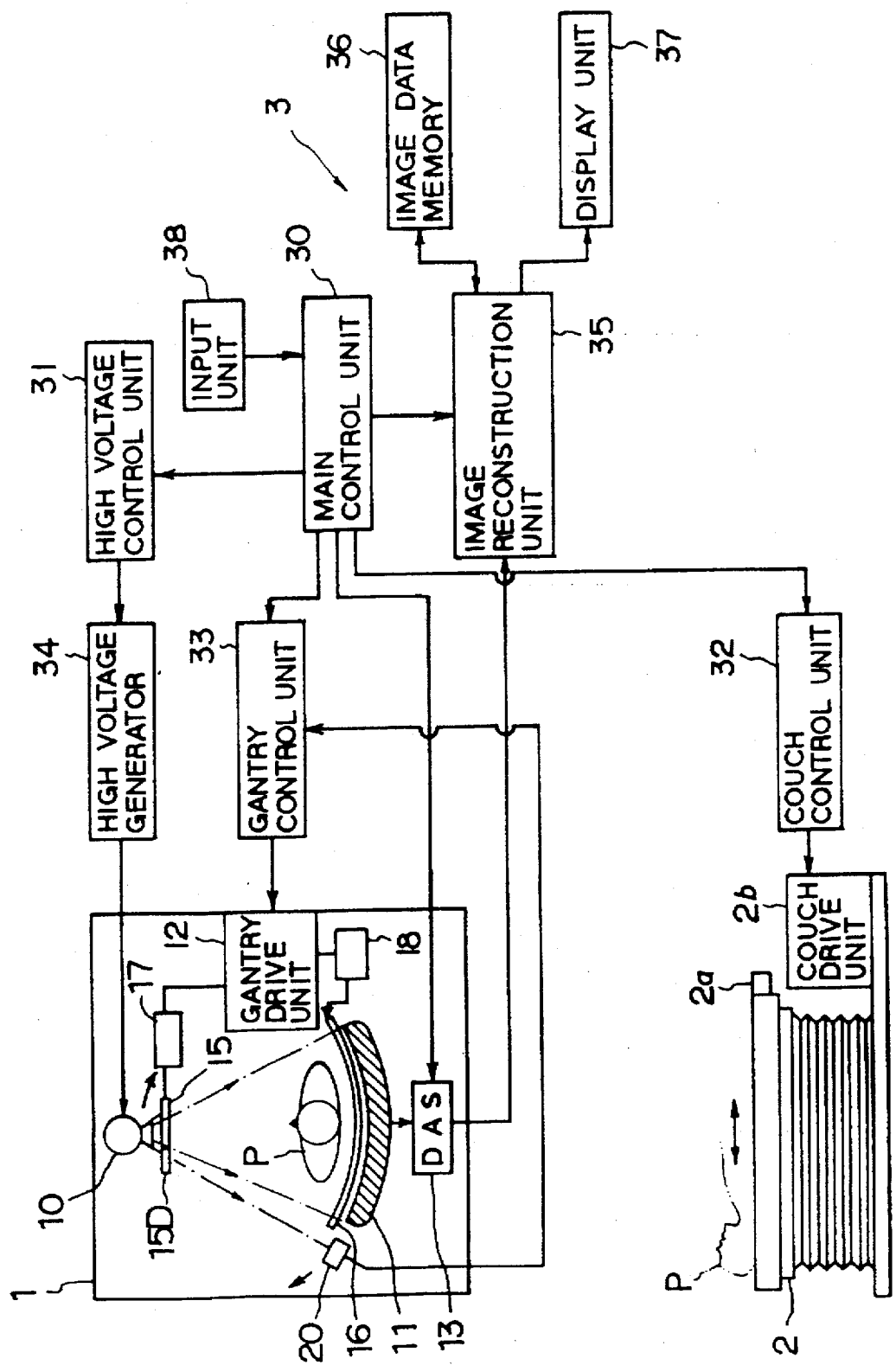
FIG. 7 is a block diagram showing an X-ray CT scanner of an embodiment of the present invention.

An X-ray CT scanner shown in FIG. 7 has a gantry 1, patient couch 2, and control cabinet 3 and is of a rotate-rotate driving type. On the top of the patient couch 2, a couchtop 2a is mounted in a state in which the couchtop 2a can slide in a longitudinal direction (equivalent to a slice (rotation-axis) direction) of the patient couch. A patient P lies down on the couchtop 2a. When driven by a couch drive unit 2b that is typically a servo motor, the couchtop 2a is inserted in a diagnostic opening of the gantry 1 so that it can advance or withdraw. The diagnostic opening includes an imaging space. The patient couch 2 is provided with a position detector (not shown) such as an encoder for detecting the position of the couchtop 2a in the longitudinal direction of the couch by means of electrical signals. A channel direction is set to be orthogonal to the slice direction.

The gantry 1 has an X-ray tube 10 and X-ray detector 11 which are opposed to each other with the patient P inserted in the opening between them. The X-ray detector 11 may be a two-dimensional detector in which a plurality of detecting device arrays each including a plurality of detecting channels are arranged in the slice direction, or a single-slice detector in which one detecting device array including a plurality of detecting channels is arranged in the slice direction. The X-ray tube 10 and X-ray detector 11 can be rotated about the rotation-axis direction in the gantry 1 by means of a gantry drive unit 12. Electrical signals equivalent to transmitted X rays detected by the X-ray detector 11 are converted into digital quantities by a data acquisition system (DAS) 13, and then sent to the control cabinet 3.

In the gantry 1, a pre-collimator 15 is interposed between the X-ray tube 10 and patient P, and a post-collimator 16 is interposed between the patient P and X-ray detector 11. The pre-collimator 15 has two blades forming a slit-like aperture whose width is constant in the channel direction and variable in the slice direction. The two blades move symmetrically in the slice direction. The whole pre-collimator 15 is movable in the slice direction. The aperture width and position in the slice direction of the pre-collimator 15 are adjusted by a pre-collimator drive unit 17 incorporated in the gantry 1. Owing to the pre-collimator drive unit 17, the width in the slice direction of an X-ray beam irradiated by the X-ray tube 10 is restricted in order to form a fan beam of a desired width. A focal spot F in the X-ray tube 10 has a finite length in the slice direction. As described previously, therefore, an umbra and penumbrae are formed as an X-ray profile in the slice direction on the detector.

Since the pre-collimator 15 is formed into a slit-like aperture shape, there are no problems concerning the penumbrae in the channel direction.

The post-collimator 16 also has a slit-like aperture whose width is constant in the channel direction and variable in the slice direction. The width in the slice direction is adjusted by a post-collimator drive unit 18. The post-collimator 18 in this embodiment fulfills the supplemental beam restriction ability to restrict an X-ray beam, which has been collimated by the pre-collimator 15, more finely.

The pre-collimator drive unit 17 and post-collimator drive unit 18 each have a stepping motor or sliding mechanism so as to operate in response to a drive control signal sent from the gantry drive unit 12. At least, the pre-collimator drive unit 17 includes a motor for use in adjusting the width of the aperture and another motor for use in adjusting the position in the slice direction of the whole aperture width.

Figure 8:
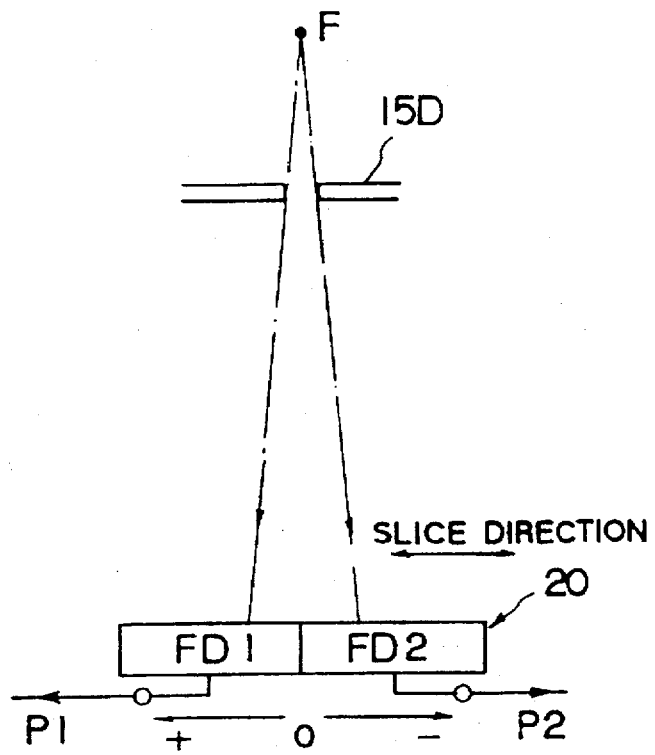
FIG. 8 is a diagram for explaining the relationship between an X-ray detector and entrance of an X-ray beam.

A focus position detector 20 serving as a focus position sensor is mounted in the vicinity of the X-ray detector 11. Part of an X-ray beam emanating from the X-ray tube 10 passes through a pre-collimator 15D designed for focus position detection and mounted on the lateral side in the channel direction of the pre-collimator 15, and then enters the focus position detector 20. The focus position detector 20 is, as shown in FIG. 8, composed of two X-ray detectors FD1 and FD2 (each having a scintillator and photodiode) which are mutually adjoining in the slice direction. Similarly to a data acquisition system, the focus position detector 20 performs A/D conversion. A resultant digital signal is sent to a gantry control unit, which will be described later, incorporated in the control cabinet 3.

Figure 9:
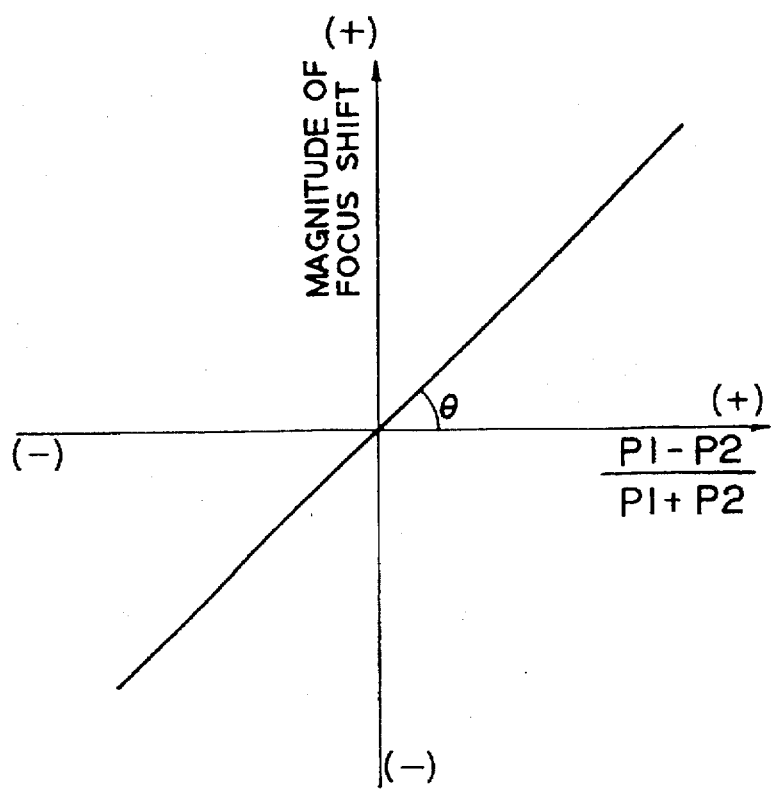
FIG. 9 is a graph plotting the relationship between outputs of an X-ray detector and magnitudes of a focus shift.

The control cabinet 3 includes a main control unit 30 for organizing the whole system as well as a high-voltage control unit 31, couch control unit 32, and gantry control unit 33 which are actuated in response to a command sent from the main control unit 30. Above all, the gantry control unit 33 computes a ratio of strengths of detection signals P1 and P2; that is, a ratio of intensities of X rays entering the two X-ray detectors FD1 and FD2 incorporated in the focus position detector 20, "(P1–P2)/(P1+P2)." Moreover, the gantry control unit 33 references a memory table, in which the values of the ratio are associated in advance with the magnitudes of a focus shift in the slice direction, so as to retrieve a magnitude of a focus shift. FIG. 9 is a graph plotting an example of the relationship between the ratio and magnitude. In a certain range of a focus shift, the relationship becomes substantially linear.

Instead of the memory table to be referenced, an expression representing the linear relationship of characteristic shown in FIG. 9 may be stored in the gantry control unit 33. A magnitude of a focus shift may then be obtained by computation.

The control cabinet 3 includes a high-voltage generator 34 that is actuated in response to a drive signal sent from the high-voltage control unit 31 shown in FIG. 7. A high voltage generated by the high-voltage generator 34 is fed to the X-ray tube 20. The control cabinet 3 comprises an image reconstruction unit 35 for reconstructing image data on receipt of an acquisition signal sent from the data acquisition system 12, an image data memory 36 for storing image data, a display unit 37 for displaying a reconstructed image, and an input unit 38 necessary for an operator to give a command to the main control unit 30.

Figure 10:
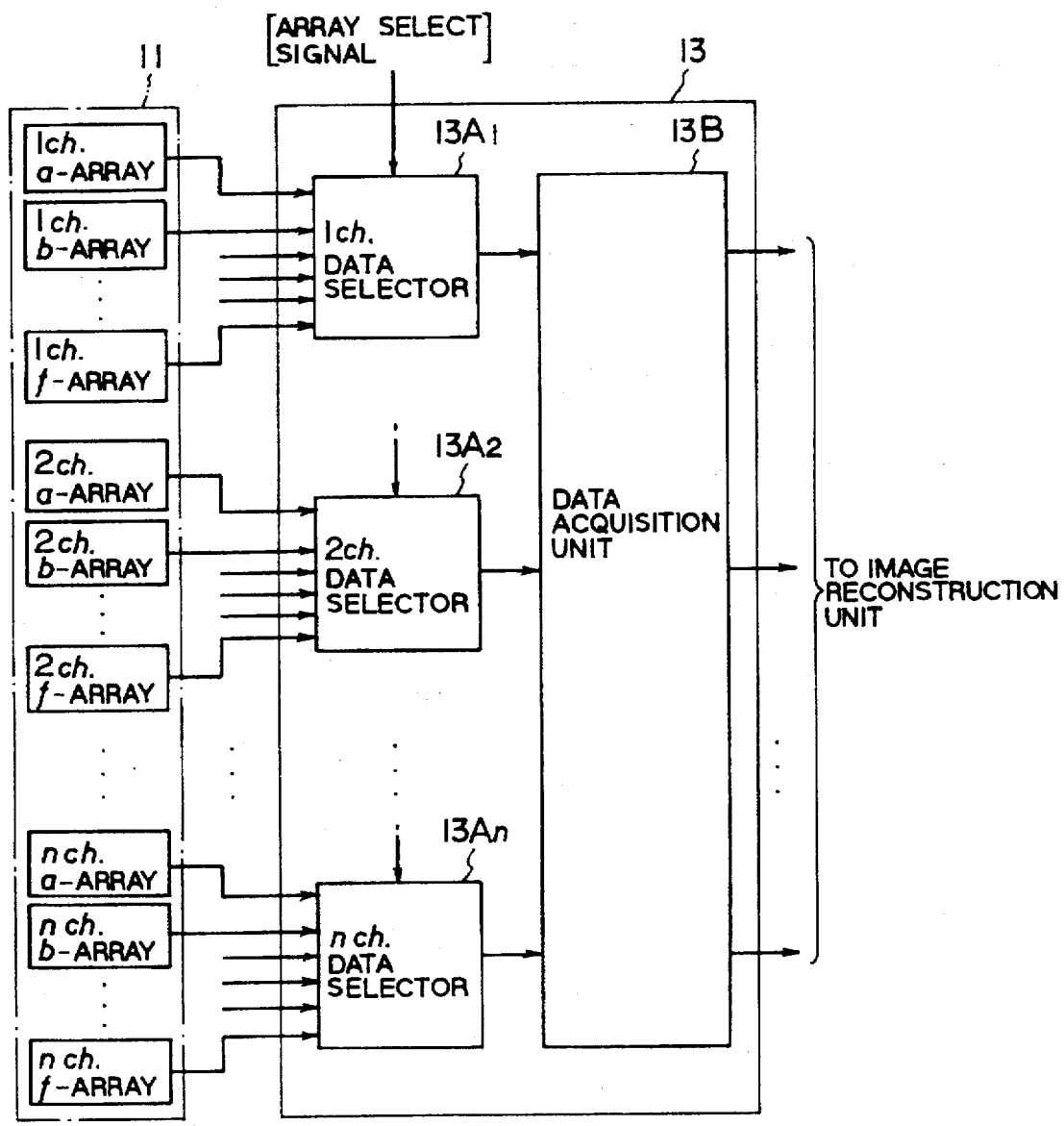
FIG. 10 is a block diagram showing a data acquisition system.

The data acquisition system 13 includes, as shown in FIG. 10, data selectors $13A_1$, $13A_2$, ..., and $13A_n$ that, when the X-ray detector 11 is a two-dimensional detector, select an array of detection signals from m detection signals, where m denotes a product of "n channels by f arrays" (where n and f denote positive integers larger than 1), for each associated channel in response to an array select signal; and a data acquisition unit 13B for amplifying detection signals selected by the data selectors $13A_1$, $13A_2$, ..., and $13A_n$ or converting them into digital signals. The array select signal is sent from the main control unit 30. X-ray detection data produced for each channel by the data acquisition unit 13B is output to the image reconstruction unit 35.

The main control unit 30 manages the whole scanner according to a predetermined procedure. An example of the procedure is described in FIGS. 11 to 14. Control given by the main control unit 30 when a two-dimensional detector is used as the X-ray detector 11 differs from that given when a single-slice detector is used.

Figure 11:
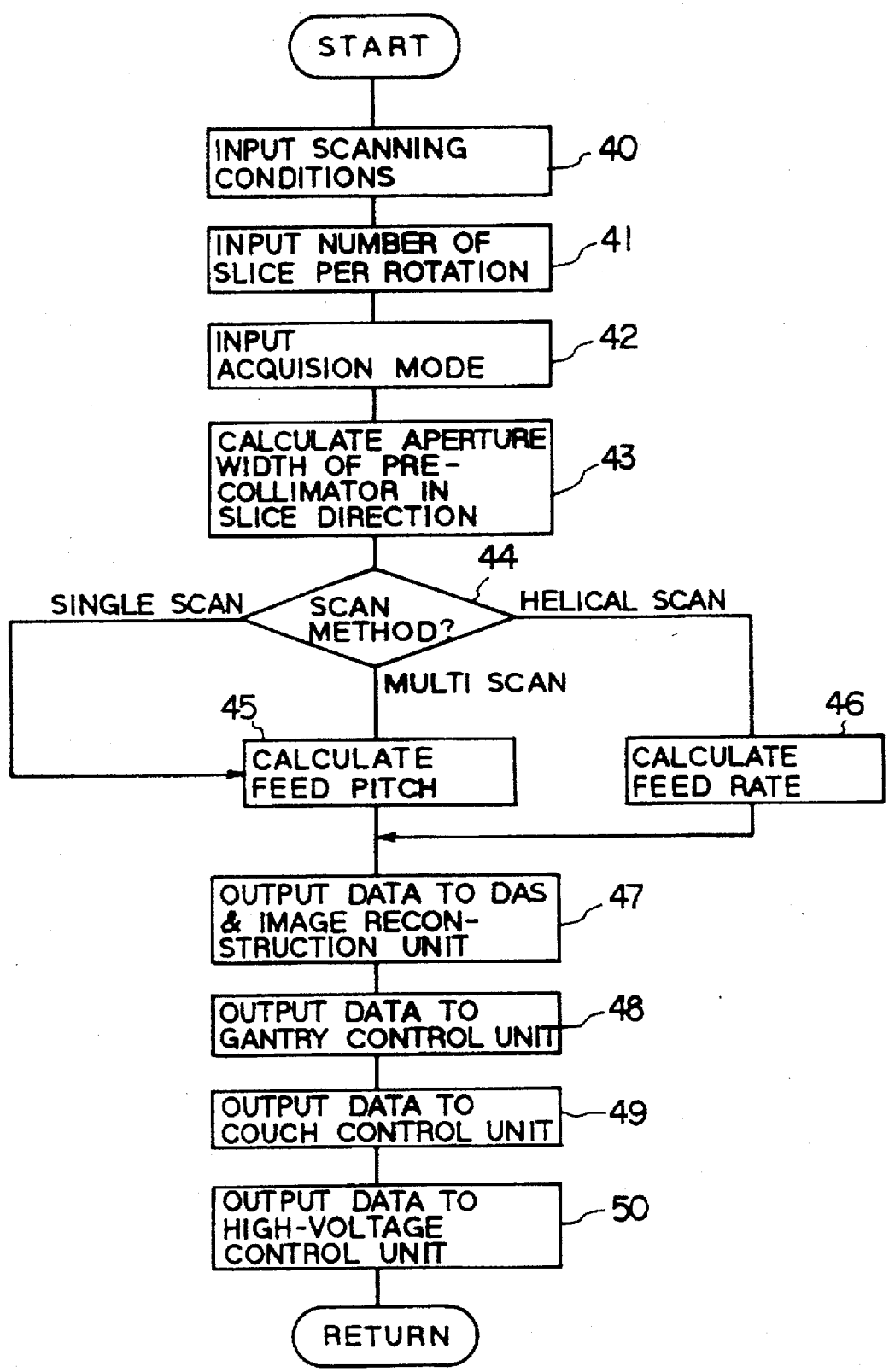
FIG. 11 is a flowchart describing an example of control executed by a main control unit when a two-dimensional detector is employed.

FIG. 11 shows an example of control given by the main control unit 30 when a two-dimensional detector is used as the X-ray detector 11.

First, at step 40, the main control unit 30 inputs scanning conditions including a scan mode (multi-scan or helical scan), the number and positions of detecting device arrays designated for data acquisition, a region and position to be scanned, a slice thickness, and an X-ray tube voltage and current (however, "the number of slices per rotation" and "acquisition mode" which will be described later are not included). At step 41, the number of slices per rotation is input. At step 42, an acquisition mode (in this embodiment, either an "umbra mode" (mode in which an umbra alone is used for data acquisition) or "umbra-plus-penumbra mode" (mode in which the umbra and (part of) penumbrae are used for data acquisition), is input. In particular, the above designated detecting element arrays are specified beforehand by an operator.

Control is then passed to step 43. The width in the slice direction of the aperture of the pre-collimator 15, $W_{pre}$, is computed. During the computation, a positional relationship the pre-collimator 15 will have is judged as described in FIG. 12.

Figure 12:
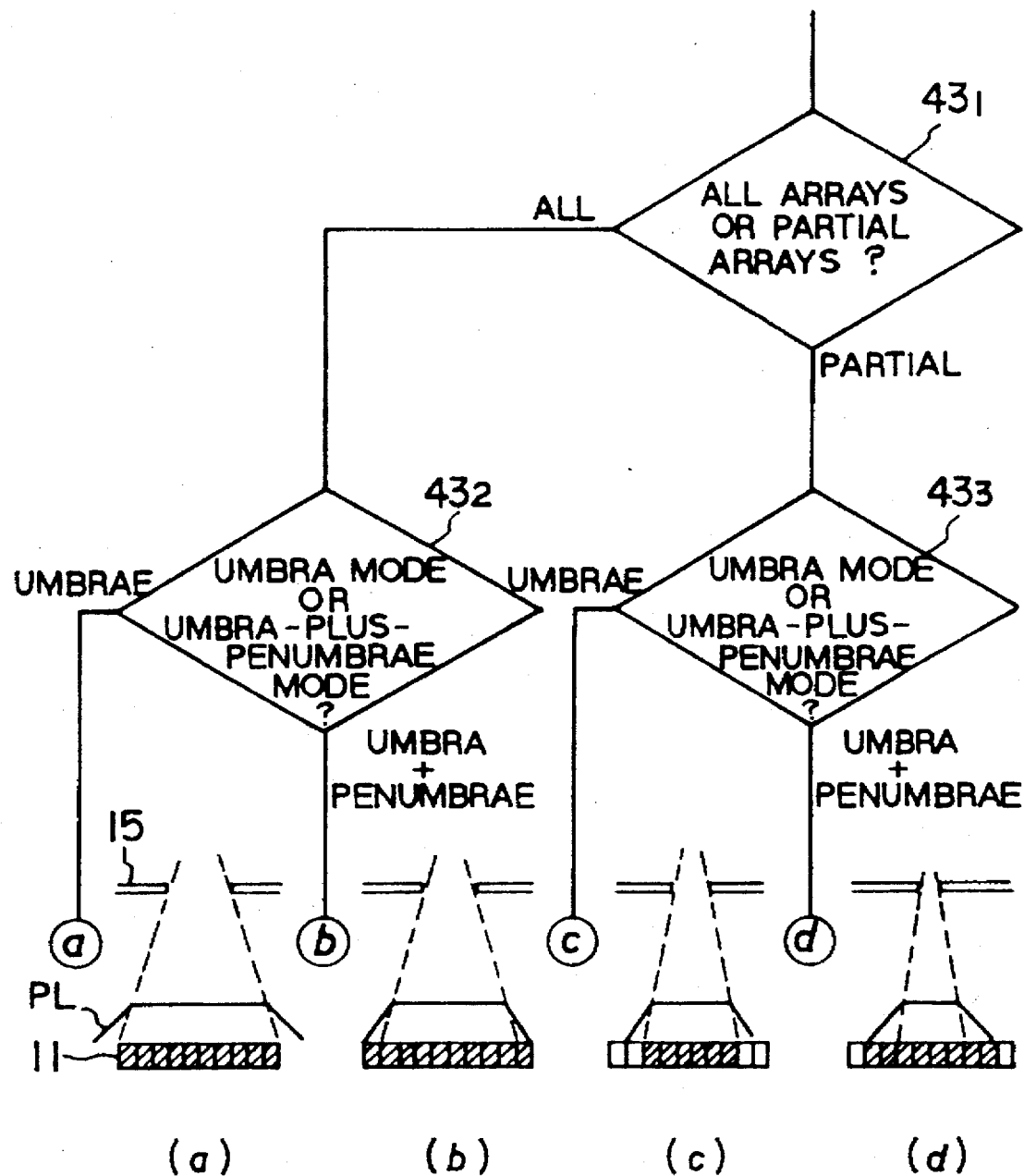
FIG. 12 is a flowchart describing a sequence for judging the positional relationship of a pre-collimator when the two-dimensional detector is employed.

More specifically, "whether all or some of a plurality of detecting device arrays in a two-dimensional detector are put to use" is judged on the basis of input information (step 40 in FIG. 11) representing a command entered at the input unit 38 (step $43_1$ in FIG. 12). If it is judged that "all of the arrays" are used, it is then judged on the basis of the input information representing a command entered at the input unit 38 whether an acquisition mode is the "umbra mode" or "umbra-plus-penumbra mode" (step $43_2$ in FIG. 12). If it is judged that the "umbra mode" has been designated, the aperture width in the slice direction of the pre-collimator 15 is controlled so that all the device arrays of the X-ray detector 11 will be covered by the umbra of an X-ray profile PL. Consequently, the pre-collimator 15, X-ray profile PL, and X-ray detector 11 have the positional relationship shown in an explanatory diagram (a) in FIG. 12. When it is judged that the "umbra-plus-penumbra mode" has been designated, penumbrae enter all the device arrays; that is, the positional relationship shown in an explanatory diagram (b) in FIG. 12 is established.

If it is judged at step $43_1$ that some, but not all, designated device arrays are used, control is passed to step $43_3$. A judgment is made in the same manner as that at step $43_2$. When this results in the "umbra mode," as shown in an explanatory diagram (c), the aperture width in the slice direction of the pre-collimator 15 is controlled so that the umbra will cover some designated detecting device arrays alone. When the "umbra-plus-penumbra mode" has been designated, penumbrae enter part of the some designated device arrays; that is, the positional relationship shown in an explanatory diagram (d) is identified.

After a positional relationship the pre-collimator 15 will have is determined to be any of those shown in the explanatory diagrams (a) to (d), the main control unit 30 computes the width in the slice direction of the aperture of the pre-collimator 15, $W_{pre}$. The computation is achieved preferably by referencing a memory table that is preset for each of the above positional relationships on the basis of position data concerning the X-ray tube 10, pre-collimator 15, isocenter in a patient, and X-ray detector. Alternatively, calculation may be performed without the use of the memory table.

Figures 18A, 18B:
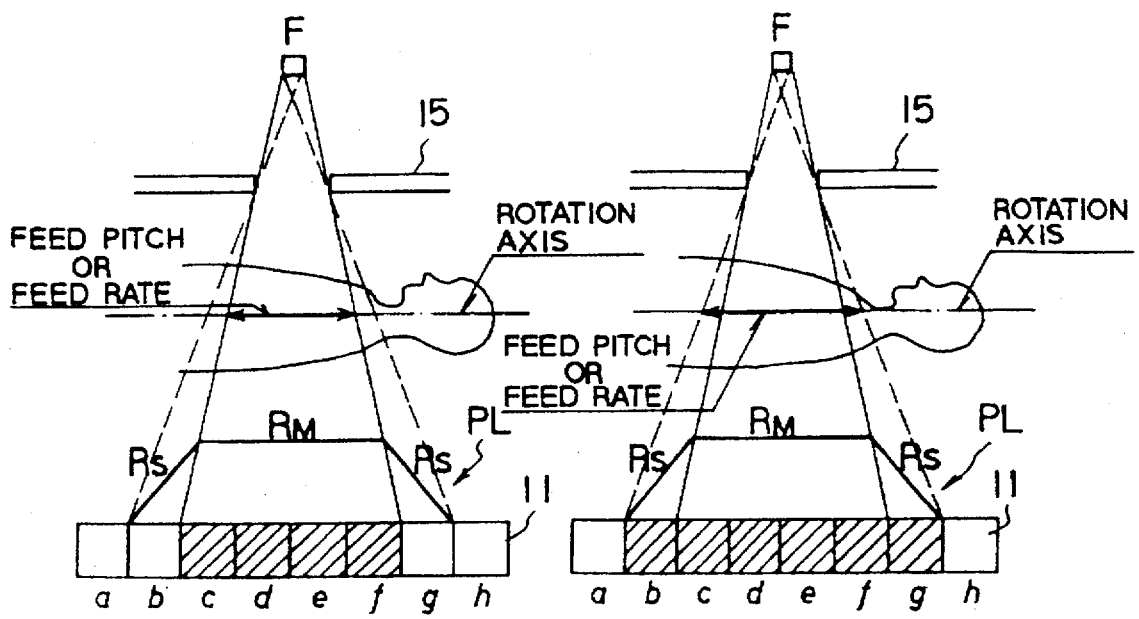
FIGS. 18A and 18B are diagrams for explaining a difference in feed pitch or feed rate between the umbra mode and umbra-plus-penumbra mode.

At step 44 in FIG. 11, a scanning technique already designated is checked. When the multi-scan has been designated, a feed pitch of the couchtop is computed at step 45. As illustrated in FIG. 18A or 18B, the feed pitch is a distance moved by the couchtop and is coincident with the total slice width of the designated detecting device arrays of the X-ray detector 11 at a center position (i.e. at the position of the rotation axis) in the diagnostic opening, the designated detecting device arrays being utilized. For helical scan, the couchtop feed rate is computed at step 46. When a feed rate is regarded as a moved distance of the couchtop per rotation, the moved distance equates to a length coincident with the total slice width of the designated detecting device arrays of the X-ray detector 11 at a center position (i.e. at the position of the rotation axis) in the diagnostic opening. In particular, another specification fashion of the feed rate may be given to the helical scan. For example, in order to enhance sampling densities in the slice direction, it is possible to select arbitrary quantities with decimal points as the feed rate, instead of the exact quantities corresponding to the designated detecting device arrays.

Multi-scan is a technique of repeating the cycle of a "scan, couchtop movement, scan, couchtop movement, etc." When the magnitude of a couchtop movement is made equal to a total slice width (i.e., a half-value width of the X-ray profile entering into all the designated detecting device arrays) attained per scan at a center position (i.e. at the position of the rotation axis) in the diagnostic opening corresponding to the designated detecting device arrays, produced images are continuous and represent equidistant and contiguous regions. Each pair of images is therefore gapless. The same applies to single-slice CT and multi-slice CT. This feature is advantageous for creating a three-dimensional model using the produced images.

Helical scan is a scanning technique of concurrently performing a scan and couchtop movement and intended to acquire data helically. For reconstructing an image, a method of interpolating acquired data as coefficients using distances from a section, of which image data is to be reconstructed, is commonly adopted. In helical scan, when a moving speed of the couchtop corresponds with a total slice width per scan at a center position (i.e. at the position of the rotation axis) in the diagnostic opening corresponding to the designated detecting device arrays, regions of data acquisition get mutually contiguous as rotations are made consecutively. Patient data can be acquired without a missing data item.

After various kinds of data are acquired as mentioned above, the main control unit 30 outputs necessary data to each of the data acquisition system 13 and image reconstruction unit 35, gantry control unit 33, couch control unit 32, and high-voltage control unit 31 (refer to steps 47 to 50). This causes the control units to operate according to pre-stored given procedures. Thus, commanded scanning is executed.

Figure 13:
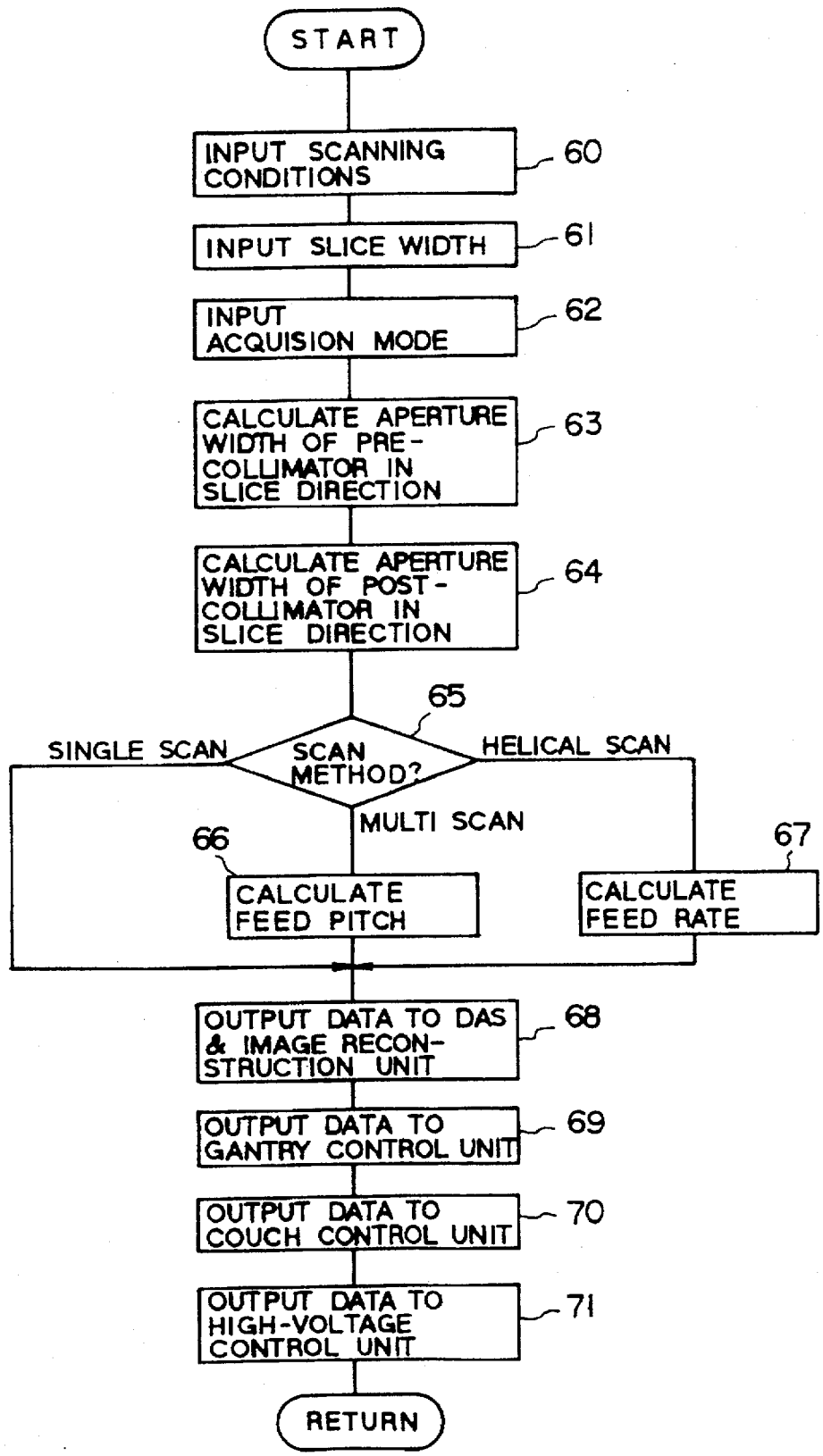
FIG. 13 is a flowchart describing an example of control executed by the main control unit when a single-slice detector is employed.

FIG. 13 describes an example of control given by the main control unit 30 when a single-slice detector is used as the X-ray detector 11. This example of control greatly differs from the one given when a two-dimensional detector is used in that information unique to single-slice CT (slice width) is acquired, and the post-collimator 16 which is not an object of control when a two-dimensional detector is used, is controlled according to the positional relationship established.

To be more specific, at step 60, the main control unit 30 inputs scanning conditions including a scan mode (single-scan, multi-scan, or helical scan), a region and position to be scanned and an X-ray tube voltage and current (however, the "slice width" and "acquisition mode" which will be described later are not included). At step 61, a slice width for single-slice scanning is input. At step 62, an acquisition mode ("umbra mode" or "umbra-plus-penumbra mode" as described previously) is input.

Control is then passed to step 63. The aperture width in the slice direction of the pre-collimator 15, $W_{pre}$ is computed. Even in this case, a positional relationship the pre-collimator 15 will have is judged as described in FIG. 14.

Figure 14:
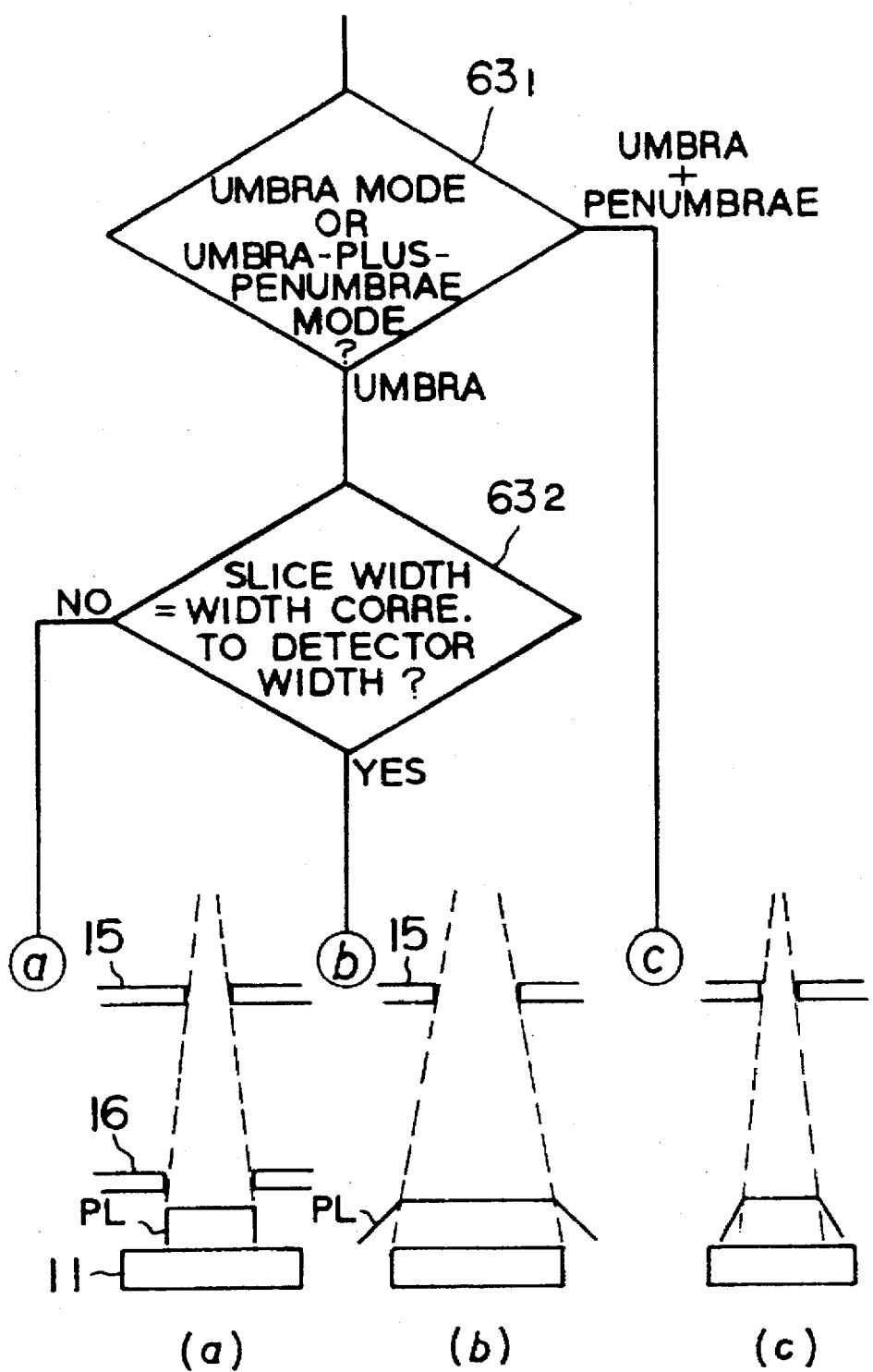
FIG. 14 is a flowchart describing a sequence for judging the positional relationship of the pre-collimator when the single-slice detector is employed.

Specifically, it is judged whether an already-input acquisition mode (step 62) is the "umbra mode" or "umbra-plus-penumbra mode" (step $63_1$ in FIG. 14). If it is judged that the "umbra mode" has been designated, control is passed to step $63_2$. It is then judged whether or not a designated slice width (step 61) equals to an width corresponding to a detector width in the rotation axis. If the judgment is in the negative, the designated slice width is smaller than the width corresponding to the detector width. A positional relationship established at this time is as shown in FIG. 14(a). This is the only case in which the post-collimator 16 is involved. By contrast, if the judgment is in the affirmative; that is, if the designated slice width equals to the width corresponding to the detector width, the pre-collimator 15 has the positional relationship shown in FIG. 14(b). If it is judged at step $63_1$ that the "umbra-plus-penumbra mode" has been designated (in this case, the designated slice width cannot equal to the width corresponding to the detector width), the positional relationship shown in FIG. 14(c) is set up. In the positional relationship shown in FIG. 14(b) or 14(c), the post-collimator 16 is not involved. What is termed the slice width here is defined as a "width obtained by projecting a half-value width of an X-ray profile on the center of the rotation axis."

The computation of the aperture width $W_{pre}$ of the pre-collimator 15 is achieved by referencing a memory table preset for each of the aforesaid positional relationships on the basis of the position data and other information concerning the X-ray tube 10, pre-collimator 15, isocenter in a patient, and X-ray detector 11. Needless to say, the aperture width $W_{pre}$ may be obtained by performing calculation every time it is needed.

At step 64 in FIG. 13, the aperture width in the slice direction of the post-collimator 16, $W_{post}$, is computed. This computation is performed only when the positional relationship shown in FIG. 14(a) is set up (in other words, only when the slice width is smaller than the width corresponding to the detector width). The aperture width $W_{post}$ is computed so that the post-collimator 16 will cut off penumbrae.

The main control unit 30 passes control to step 65 and judges a scanning technique. If it is judged that single-scan has been designated, control is skipped to step 68. If it is judged that multi-scan or helical scan has been designated, a feed pitch or feed rate of the couchtop is computed with the slice width taken into account at step 66 or 67.

Thereafter, the processing of steps 68 to 71 is executed sequentially in the same manner as that of steps 47 to 50 in FIG. 11.

An example of aperture width control in the slice direction of the collimator 15 or 16 which is given by the gantry control unit 33 will be described in conjunction with FIG. 15.

Figure 15:
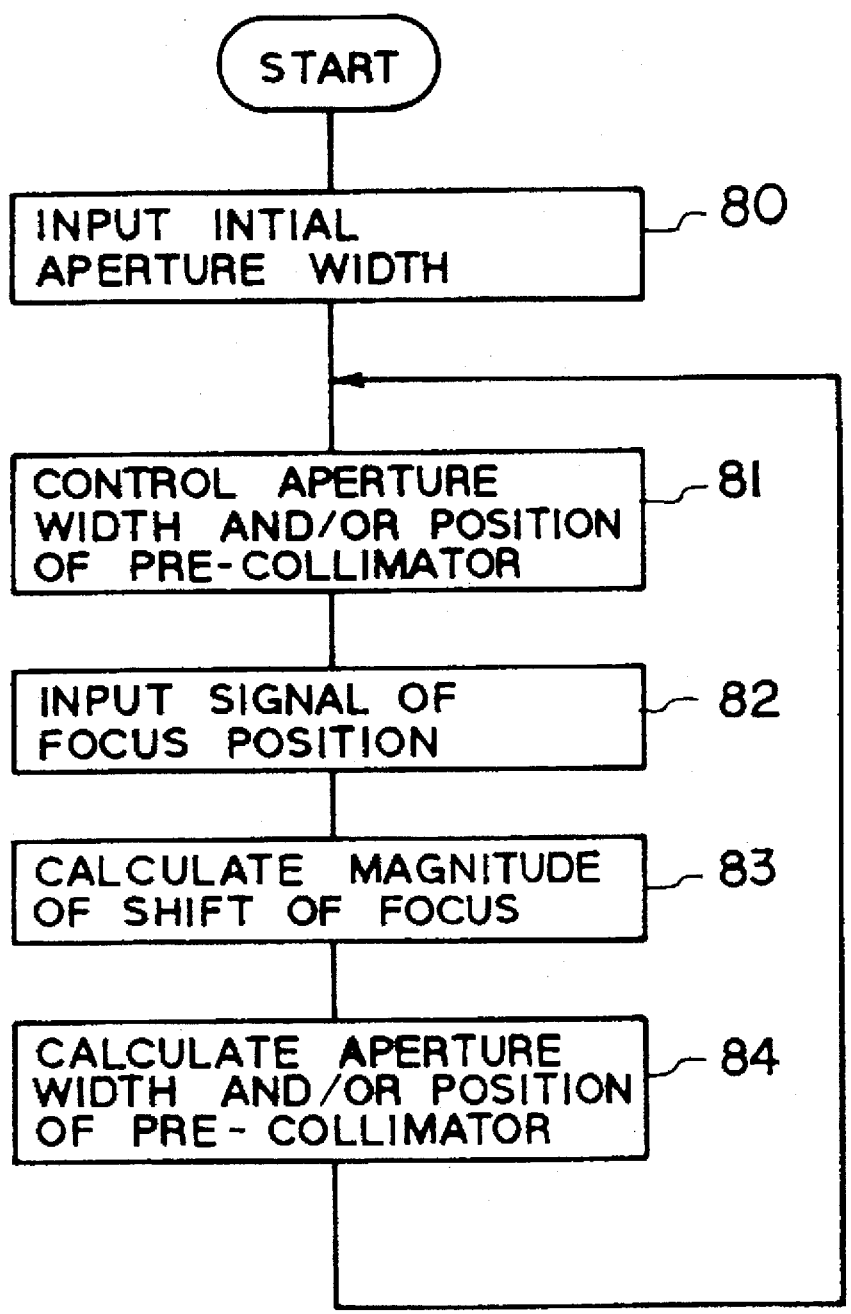
FIG. 15 is a flowchart describing an example of aperture control executed by a gantry control unit.

The gantry control unit 33 inputs an aperture width $W_{pre}$ supplied from the main control unit as one of initial values (step 80 in FIG. 15). The gantry control unit 33 sends a control signal associated with the input data to the gantry drive unit 12 so as to actuate the pre-collimator drive unit 17. The actual aperture width and/or position in the slice direction of the pre-collimator 15 are then agreed with the commanded initial values (step 81 in FIG. 15).

Thereafter, a detection signal sent from the focus position detector 20 is input (step 82 in FIG. 15). The magnitude of the shift of the focal spot F resulting from heat dissipation etc. occurring in the X-ray tube 10 is computed (step 83 in FIG. 15).

Control is then passed to step 84. The aperture width $W_{pre}$ and/or position in the slice direction of the pre-collimator 15 is computed again with the predicted magnitude of the shift of the focal spot F taken into account. This results in aperture data used to compensate for a movement in the slice direction of the X-ray profile PL caused by the shift of the focal spot F. The new data for compensation is sent to the gantry drive unit 12. Using the updated value, the aperture width and/or position of the pre-collimator 15 is corrected (step 81 in FIG. 15). Thereafter, the aforesaid sequence is repeated.

In the focus lock-on control for coping with a focus shift which relates to the processing described in FIG. 15, the pre-collimator 15 alone should be locked on to the focal spot. The post-collimator 16 need not be locked on to the focal spot because it lies close to the X-ray detector 11. When a single-slice detector is adopted as the X-ray detector 11, if the pre-collimator 15 has a positional relationship satisfying the condition that a slice width is smaller than a detector width (the positional relationship shown in FIG. 14(a)), it is commanded through processing, which is not shown, executed by the gantry control unit 33 that the post-collimator 16 should have the aperture width $W_{post}$ computed by the processing of step 64 in FIG. 13. However, even in this case, the aperture width $W_{post}$ of the post-collimator 16 is retained at a fixed value all the time so that penumbrae can be cut off but not subjected to lock-on control despite a focus shift. When the pre-collimator 15 has any other positional relationship; that is, any of the positional relationships shown in FIGS. 12(a) to 12(d) and 14(b), and 14(c), the post-collimator 16 is not involved in X-ray collimation.

Figure 16:
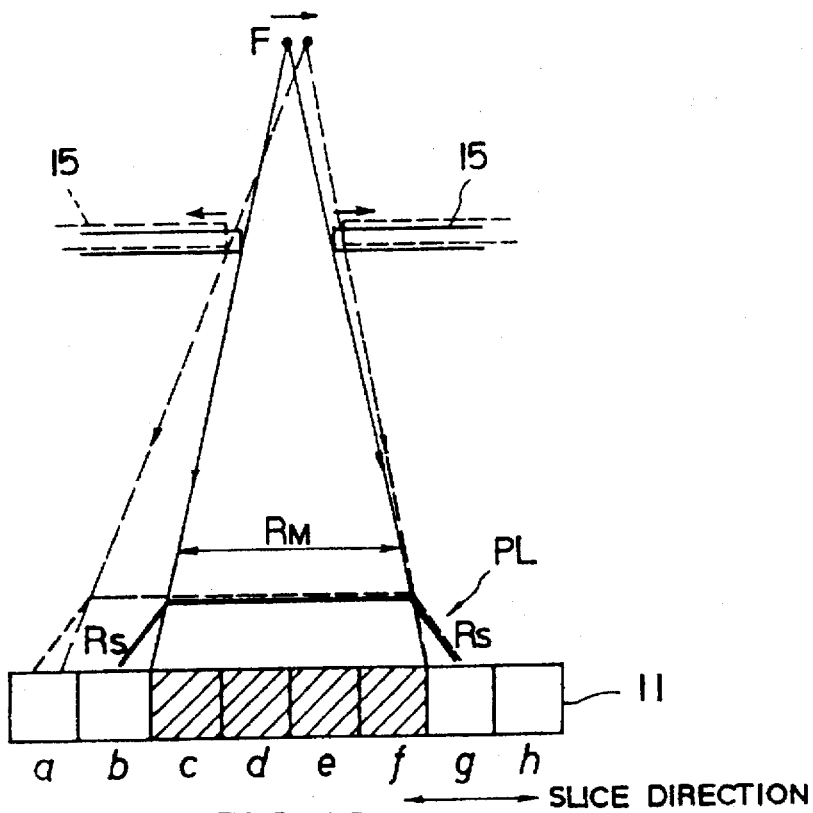
FIG. 16 is an explanatory diagram showing an example of focus shift lock-on control executed when a two-dimensional detector is used.
Figure 17:
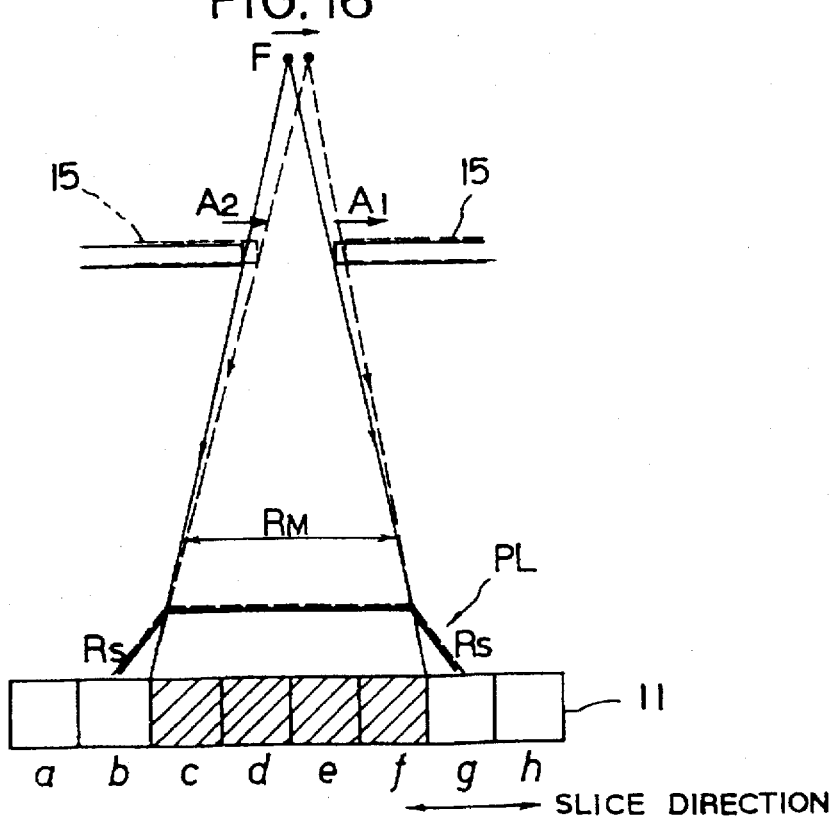
FIG. 17 is an explanatory diagram showing another example of focus shift lock-on control executed when the two-dimensional detector is used.

Examples of operations relating to the aforesaid configuration and processing are shown in FIGS. 16 and 17. FIG. 16 shows an example of controlling only the aperture width of the pre-collimator 15. FIG. 17 shows an example of controlling the aperture width and position in the slice direction of the pre-collimator 15.

Assume that a two-dimensional detector is used as the X-ray detector 11 (device arrays a to h shall be arranged in the slice direction), and some of the detecting device arrays are arranged in the slice direction; that is, device arrays c to f are designated to execute multi-scan in umbra mode. After scanning conditions including this information, the number of slices, and an acquisition mode are input to the main control unit 30 (steps 40 to 41 in FIG. 11), the positional relationship and aperture width in the slice direction of the pre-collimator 15 are determined automatically (step 43 in FIG. 11). Since multi-scan is commanded as a scanning technique, a feed pitch is automatically computed so that it will be equal to a total slice width corresponding to the some designated device arrays (step 45 in FIG. 11). Data items that have thus been input and computed are consecutively output to the data acquisition system 13, image reconstruction unit 35, gantry control unit 33, couch control unit 32, and high-voltage control unit 31 respectively.

Above all, the data acquisition system 13 switches arrays for each channel in response to an array select signal indicating which array (in this case, which of the arrays c to f) should be used in compliance with a command issued from the main control unit 30, selects necessary data, and sends the data to the image reconstruction unit 35. Since multi-scan is commanded, a slice width corresponding to the arrays c to f is set as a feed pitch of the couchtop. When helical scan is commanded, the slide width corresponding to the arrays c to f is set as a distance moved by the couchtop during one rotation. All trajectories traced by the detector are therefore equidistant. Consequently, data compensation and other processing required for image reconstruction become simpler.

As a result, under the management of the main control unit 30, the respective units operate mutually synchronously so as to acquire data and reconstruct images represented by the data. At this time, the pre-collimator 15 has the positional relationship shown in FIG. 16 (equivalent to FIG. 12(c)). In other words, the aperture width $W_{pre}$ in the slice direction of the pre-collimator 15 is controlled so that only the umbra $R_M$ will enter the designated ones c to f of the detecting device arrays a to h in the two-dimensional detector 11.

The focal spot F in the X-ray tube 10 may be, as shown in FIG. 16, shifted in the slice direction due to heat dissipation etc. occurring at the time of electron impingement of the anode. Even in this case, the aperture width of the pre-collimator 15 is finely adjusted in real time by the processing in FIG. 15 accompanying detection of the magnitude of a focus shift. Consequently, the umbra $R_M$ alone enters the designated device arrays c to f that are some of the detecting device arrays.

Since the aperture width of the pre-collimator 15 is controlled and fed back as mentioned above, even when an X-ray profile formed during actual scanning differs from the one formed during calibration data acquisition, the intensities of X rays entering the designated detecting device arrays c to f (the slice width in the slice direction) of the two-dimensional detector 11 which have been predetermined to be used are constant all the time. Good calibration can therefore be applied during reconstruction. Consequently, occurrence of artifacts in an image or shifts of CT numbers which have occurred in the past can be prevented. A demand for coping with a change of an X-ray profile can be alleviated drastically. Since a reconstructed image results from an umbra alone, the quality of an image of any slice section is good. Furthermore, since only the aperture width of the pre-collimator 15 should be controlled, only one motor will be driven, to be employed in aperture width control. This provides the merit of simplified control.

The control procedure described in conjunction with FIG. 16 can preferably apply to a technique in which the whole surface of a two-dimensional detector is used, as in the example of FIG. 16, for instance, wherein all of the detecting device arrays a to h are used to perform scanning in umbra mode (that is, in the state shown in FIG. 12(a)). When a single-slice detector is used as the X-ray detector 11, if scanning is performed in umbra mode (that is, the state shown in FIG. 14(a) or 14(b)), the control procedure can be implemented preferably.

For scanning shown in FIG. 17, the same conditions as those for scanning shown in FIG. 16 (employment of a two-dimensional detector, use of some designated ones of detecting device arrays arranged in the slice direction; that is, only the designated detecting device arrays c to f, adoption of the umbra mode) are adopted. The quantity of feedback control for coping with a focus shift is determined with the "positions in the slice direction" of the blades (that is, the aperture width and position in the slice direction of the pre-collimator). In short, the position in the slice direction of the whole pre-collimator 15 is changed in real time. This control is effected in real time by the sequence of steps 82 to 84 and 81 in FIG. 15.

Assuming that the focal spot F in the X-ray tube 10 shifts rightward in a direction of an arrow in FIG. 17, one of the blades of the pre-collimator 15 lying in the slice direction is moved rightward (arrow $A_1$), and the other blade is also moved rightward by the same distance. In other words, unlike the control effected when both the blades responsible for collimation in the slice direction move, as shown in FIG.

16, symmetrically in the slice direction so as to vary the aperture width $W_{pre}$ alone, this control is effected to change the aperture width $W_{pre}$ and the position in the slice direction of the whole collimator according to the magnitude of a focus shift.

The position in the slice direction of the X-ray profile PL relative to the X-ray detector 11 remains unchanged. Even if a focus shift occurs actually, it is handled in the same manner as a nominal focus shift occurs. The same effect and advantage as those available in the procedure described in conjunction with FIG. 16 are provided. Compared with the procedure of FIG. 16, the foregoing procedure has the merits that the position of a profile can be controlled more stably with higher precision, and that a patient exposure can be minimized. More important, for pre-collimator control in FIG. 17, the positions of the penumbrae in the slicing direction can be fixed. This means that partial detecting device arrays receiving the penumbrae have the same form of X-ray profiles for both calibration data and image data acquisition. Therefore, there is a great advantage that image quality using data supplied from the foregoing partial detecting device arrays can be kept high.

The control procedure described in conjunction with FIG. 17 can preferably apply to a technique in which the whole surface of a two-dimensional detector is used, as in the example of FIG. 17, for instance, wherein all the detecting device arrays a to h are used to perform scanning in umbra mode (that is, in the state shown in FIG. 12(a)). When a single-slice detector is used as the X-ray detector 11, if scanning is performed in umbra mode (that is, in the state of FIG. 14(a) or 14(b)), the procedure can also be implemented preferably.

The "umbra-plus-penumbra mode" is selected by an examining physician if necessary (Refer to step 42 in FIG. 11 and step 62 in FIG. 13). Not only the "umbra mode" but also the "umbra-plus-penumbra mode" can be selected. This provides the merits that when penumbrae are allowed to enter a detector, a patient exposure can be suppressed, and multi-scan or helical scan can be achieved at a high speed. The merits are illustrated in FIGS. 18A and 18B. FIG. 18A describes "umbra-mode" scanning, while FIG. 18B describes "umbra-plus-penumbra-mode" scanning. The number of usable device arrays in the X-ray detector 11 in FIG. 18B is larger than that in FIG. 18A. This means that fast scanning is feasible in "umbra-plus-penumbra mode."

Incidentally, in FIGS. 18A and 18B, the arrows each representing the quantity of the feed pitch or feed rate is pictorially drawn; since the X-ray focus is considered as a point in those calculations, the actual quantity should be slightly smaller, but corresponds to the total slice width.

A variant in accordance with the present invention will be described in conjunction with FIG. 19. The aforesaid embodiment is configured so that the position and/or aperture width in the slice direction of the pre-collimator 15 are finely adjusted in real time according to a shift of a focal spot in an X-ray tube. In this variant, the configuration is simplified. Specifically, the aperture width and/or position in the slice direction of the pre-collimator 15 is initialized only once, and the values are held unchanged despite a focus shift.

Similarly to the aforesaid techniques adopted in FIGS. 16 and 17, some designated ones of the detecting device arrays in a two-dimensional detector; that is, the designated detecting device arrays c to e alone, are used to perform scanning in umbra mode. The aperture width $W_{pre}$ (or position) is set only once at the beginning so that even if a focus shift occurs because the X-ray tube 10 makes a transition from a state of the lowest temperature to a state of the highest temperature, an umbra alone can enter at least the designated detecting device arrays c to e without fail. In other words, a focus shift is predicted in order to determine detecting device arrays to be employed, and then an aperture width (or a position in the slice direction) is set to a rather larger value. Once the aperture width is set prior to scanning, aperture control is not performed any longer.

Figure 19:
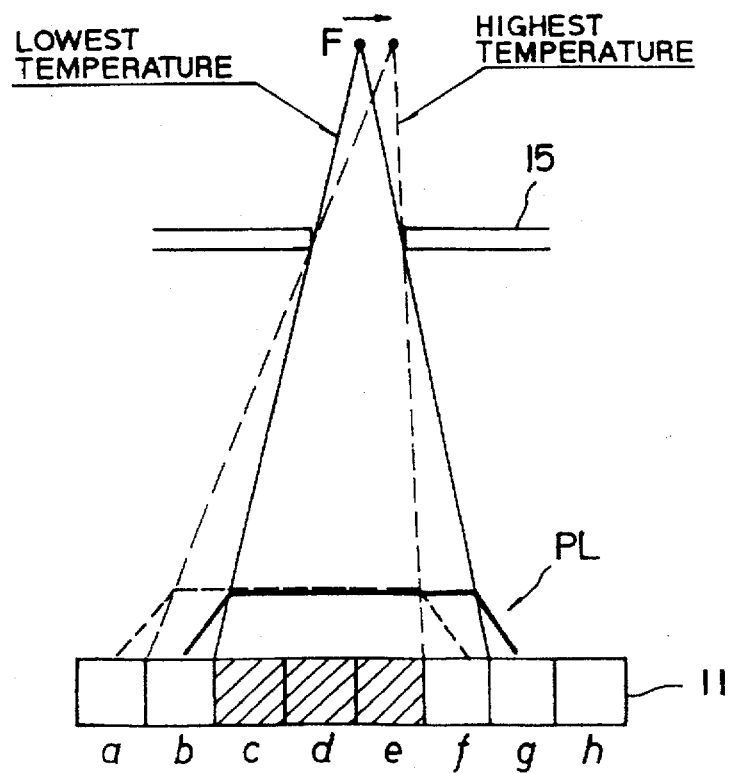
FIG. 19 is a diagram for explaining aperture setting for a pre-collimator in a variant.

Even when the temperature of an X-ray tube rises according to a driven state of an X-ray CT scanner, if a focal spot is shifted from the state indicated with a solid line in FIG. 19 to a state indicated with a dashed line (in which the X-ray tube is heated to the greatest extent), an umbra alone enters the designated device arrays c to e in the X-ray detector 11 without fail. According to this variant, aperture control is required only once. This results in simplified control. Moreover, there is the merit of obviating the necessity of the focus position detector 20.

The control procedure described in FIG. 19 can preferably apply to a technique in which the whole surface of a two-dimensional detector is used, as in the example of FIG. 19, for instance, wherein all the detecting device arrays a to h are used to perform scanning in umbra mode (that is, in the state shown in FIG. 12(a)). When a single-slice detector is used as the X-ray detector 11, if scanning is performed in umbra mode (that is, in the state shown in FIG. 14(a) or 14(b)), the control procedure can also be implemented preferably.

In the aforesaid variant, the means for initializing an aperture width (or position) of the pre-collimator 15 only once at the time of scanning need not be exploited. Alternatively, the aperture width may be set to a fixed value in advance.

A sensor means for sensing a shift of a focal spot in an X-ray tube in the present invention is not limited to the one having the aforesaid configuration. Alternatively, an infrared detector mounted, for example, on the outer circumference of the X-ray tube 10 may be used to detect a temperature change in the X-ray tube, and then a shift of a focal spot may be predicted on the basis of the temperature change. Otherwise, a temperature detector for detecting the temperature of a cooling oil in an X-ray tube may be employed. A structure for fetching information concerning driving of an X-ray tube; such as, an X-ray tube voltage, X-ray tube current, X-ray irradiation time, and X-ray irradiation stop time as information concerning a shift of a focal spot may be employed.

In the aforesaid embodiment and variant, the aperture of the post-collimator 16 is controlled only when a single-slice detector is used to perform scanning in umbra mode and a slice width becomes smaller than a detector width. The post-collimator 16 may be controlled synchronously with the pre-collimator 15 so that the post-collimator 16 can actively cut off penumbrae (in umbra mode) that are unwanted X rays entering a surface other than a housing of a detector. This makes it possible to more reliably prevent an unwanted exposure of a patient resulting from scattering of penumbrae caused by the housing of a detector or a CT gantry. The synchronous control of the post-collimator 16 obviates the necessity of a scattering prevention structure that may be an X-ray absorbent to be attached to the housing of a detector.

The present invention is not limited to the embodiments in which, when actual diagnosis is carried out, one or more detecting element arrays can be designated to the two-dimensional detector in order to receive the only penumbra of the X-ray beam. Even if the one or more detecting element arrays to be used have been predetermined in terms of design choice and other factors, such two-dimensional detectors can be preferably applied to the X-ray scanner of the invention by employing only data detected by such predetermined element arrays.

Moreover, the foregoing embodiments and those variants have been described with regard to adjustment of the physical quantities in the pre-collimator control, but alternative variations are available to such control. One example, an electron beam impinging on a target, can be controlled by electromagnetic field in the X-ray tube so that the focal spot position viewed from the outside is unchanged. Alternatively, the position of the X-ray tube itself can be moved for the same purpose.

The present invention is not limited to the foregoing embodiments and variants, and can be modified or altered without departing from the basic inventive principle.

What is claimed is:

1. An X-ray CT scanner comprising:
   an X-ray source irradiating an X-ray beam toward an object to be scanned;
   a pre-collimator being interposed between the X-ray source and the object and collimating a width of the X-ray beam in a slice direction set to the object;
   an X-ray detector receiving the X-ray beam transmitted through the object and consisting of a two-dimensional detector in which a plurality of detecting element arrays are arranged in the slice direction, each detecting element array including a plurality of detecting channels;
   means for controlling the pre-collimator in a manner that a detecting element array designated among the plurality of detecting element arrays receives an umbra of the X-ray beam, the umbra being formed by the pre-collimator together with penumbrae on a profile of the X-ray beam; and
   means for reconstructing an X-ray CT image on the basis of data detected by the designated element array.

2. The X-ray CT scanner of claim 1, further comprising:
   a gantry having an imaging space for the object; a tabletop for laying the object thereon, the tabletop being movable in the slice direction;
   means for determining a moving distance of the tabletop for every scan of the X-ray beam under a multi scan manner repeating alternately the scan and movement of the tabletop, the moving distance coinciding with a total slice width of the designated detecting element array, the total slice width being taken at a center position of the imaging space; and
   means for controlling the movement of the tabletop on the basis of the moving distance determined by the determining means.

3. The X-ray CT scanner of claim 1, further comprising:
   a gantry having an imaging space for the subject;
   a tabletop for laying the object thereon, the tabletop being movable in the slice direction;
   means for determining a moving distance of the tabletop for every one rotation of the X-ray tube and the X-ray detector around the object operated under a helical scan in association with a total width of the designated detecting element array at a center position of the imaging space in the slice direction; and
   means for controlling movement of the tabletop on the basis of the moving distance determined by the determining means.

4. The X-ray CT scanner of claim 1, further comprising
   means for widely setting an aperture width of the pre-collimator in the slice direction by a quantity corresponding to a predictable maximum quantity of movement of the X-ray beam in the slice direction depending on movement of X-ray focal spot of the source.

5. The X-ray CT scanner of claim 1, further comprising
   means for detecting a quantity corresponding to movement of a focal spot of the X-ray source,
   wherein the controlling means includes means for controlling at least one of an aperture width of the pre-collimator in the slice direction, a position of the pre-collimator in the slice direction, and a position of the focal spot of the X-ray source in the slice direction on the basis of the quantity detected by the detecting means in a manner that the designated detecting element array receives the umbra of the X-ray beam.

6. An X-ray CT scanner comprising:
   an X-ray source irradiating an X-ray beam toward an object to be scanned;
   a pre-collimator being interposed between the X-ray source and the object and collimating a width of the X-ray beam in a slice direction set to the object;
   an X-ray detector receiving the X-ray beam transmitted through the object and consisting of a two-dimensional detector in which a plurality of detecting element arrays are arranged in the slice direction, each detecting element array including a plurality of detecting channels; and
   means for reconstructing an X-ray CT image on the basis of data detected by at least one detecting element array of the plurality of detecting element arrays, the at least one detecting element array receiving an umbra of the X-ray beam, the umbra being formed by the pre-collimator together with penumbrae on a profile of the X-ray beam.

7. The X-ray CT scanner of claim 6, further comprising:
   a gantry having an imaging space for the object;
   a tabletop for laying the object thereon, the tabletop being movable in the slice direction;
   means for determining a moving distance of the tabletop for every scan of the X-ray beam under a multi scan manner repeating alternately the scan and movement of the tabletop, the moving distance coinciding with a total slice width of the at least one detecting element array, the total slice width being taken at a center position of the imaging space; and
   means for controlling the movement of the tabletop on the basis of the moving distance determined by the determining means.

8. The X-ray CT scanner of claim 6, further comprising:
   a gantry having an imaging space for the object;
   a tabletop for laying the object thereon, the tabletop being movable in the slice direction;
   means for determining a moving distance of the tabletop for every one rotation of the X-ray tube and the X-ray detector around the object under a helical scan in association with a total width of at least one detecting element array at a center position of the imaging space in the slice direction; and
   means for controlling movement of the tabletop on the basis of the moving distance determine by the determining means.

9. The X-ray CT scanner of claim 6, further comprising means for widely setting an aperture width of the pre-collimator in the slice direction by a quantity corresponding to a predictable maximum quantity of movement of the X-ray beam in the slice direction depending on movement of a focal spot of the X-ray source.

10. The X-ray CT scanner of claim 6, further comprising means for detecting a quantity corresponding to movement of a focal spot of the X-ray source; and means for controlling at least one of an aperture width of the pre-collimator in the slice direction, a position of the pre-collimator in the slice direction, and a position of a focal spot of the X-ray tube in a slice direction on the basis of the quantity detected by the detecting means in a manner that at least, the one detecting element array receives the umbra of the X-ray beam.

11. Ax X-ray CT scanner comprising:

an X-ray source irradiating an X-ray beam toward an object to be scanned;

a pre-collimator being interposed between the X-ray source and the object and collimating a width of the X-ray beam in a slice direction set to the object;

an X-ray detector receiving the X-ray beam transmitted through the object and consisting of a two-dimensional detector in which a plurality of detecting element arrays are arranged in the slice direction, each detecting element array including a plurality of detecting channels;

means for selecting either one of a first acquisition mode under which image reconstruction is carried out using data obtained in response to an only umbra on a profile of the X-ray beam formed by the pre-collimator together with penumbrae on the profile of the X-ray beam, and a second acquisition mode under which image reconstruction is carried out using data obtained in response to both the umbra and the penumbrae; and means for scanning in order to acquire the data depending on the acquisition mode selected by the selecting means.

12. The X-ray CT scanner of claim 11, further comprising:

a gantry having an imaging space for the object;

a tabletop for laying the object thereon, the tabletop being movable in the slice direction;

means for determining a moving distance of the tabletop for every scan of the X-ray beam under a multi scan manner repeating alternately the scan and movement of the tabletop, the moving distance coinciding with a total slice width of a detecting element array designated among the plurality of detecting element arrays, the total slice width being taken at a center position of the imaging space; and means for controlling the movement of the tabletop on the basis of the moving distance determined by the determining means.

13. The X-ray CT scanner of claim 11, further comprising:

a gantry having an imaging space for the object;

a tabletop for laying the object thereon, the tabletop being movable in the slice direction;

means for determining a moving distance of the tabletop for every one rotation of the X-ray tube and the X-ray detector around the object under a helical scan in association with a total width of at least one detecting element array at a center position of the imaging space in the slice direction; and means for controlling movement of the tabletop on the basis of the moving distance determined by the determining means.

14. The X-ray CT scanner of claim 11, further comprising means for widely setting an aperture width of the pre-collimator in the slice direction by a quantity corresponding to a predictable maximum quantity of movement of the X-ray beam in the slice direction depending on movement of a focal spot of the X-ray source.

15. The X-ray CT scanner of claim 11, further comprising:

means for detecting a quantity corresponding to movement of a focal spot of the X-ray source;

means for controlling at least one of an aperture width of the pre-collimator in the slice direction, a position of the pre-collimator in the slice direction, and a position of the focal spot of the X-ray source in the slice direction on the basis of the quantity detected by the detecting means so as to prevent movement of the profile of the X-ray beam entering the X-ray detector.

16. The X-ray CT scanner of claim 11, further comprising means for controlling a collimating condition of the pre-collimator in accordance with the acquisition mode selected by the selecting means.

17. The X-ray CT scanner of claim 16, further comprising:

a gantry having an imaging space for the object;

a tabletop for laying the object thereon, the tabletop being movable in the slice direction;

means for determining a moving distance of the tabletop for every scan of the X-ray beam under a multi scan manner repeating alternately the scan and movement of the tabletop, the moving distance coinciding with a total slice width of a detecting element array designated among the plurality of detecting element arrays, the total slice width being taken at a center position of the imaging space; and means for controlling the movement of the tabletop on the basis of the moving distance determined by the determining means.

18. The X-ray CT scanner of claim 16, further comprising:

a gantry having an imaging space for the object;

a tabletop for laying the object thereon, the tabletop being movable in the slice direction;

means for determining a moving distance of the tabletop for every one rotation of the X-ray tube and the X-ray detector around the object under a helical scan in association with a total width of the at least one detecting element array at a center position of the imaging space in the slice direction; and means for controlling movement of the tabletop on the basis of the moving distance determined by the determining means.

19. The X-ray CT scanner of claim 16, further comprising means for widely setting an aperture width of the pre-collimator in the slice direction by a quantity corresponding to a predictable maximum quantity of movement of the X-ray beam in the slice direction depending on movement of a focal spot of the X-ray source.

20. The X-ray CT scanner of claim 16, further comprising means for detecting a quantity corresponding to movement of a focal spot of the X-ray source, wherein the controlling means includes means for controlling at least one of an aperture width of the pre-collimator in the slice direction, a position of the pre-collimator in the slice direction, and a position of the focal spot of the X-ray source in the slice direction on the basis of the quantity detected by the detecting means so as to prevent movement of the profile of the X-ray beam entering the X-ray detector.

* * * * *